(12) United States Patent
Stinson et al.

(10) Patent No.: US 8,398,702 B2
(45) Date of Patent: Mar. 19, 2013

(54) MOLYBDENUM ENDOPROSTHESES

(75) Inventors: Jonathan S. Stinson, Plymouth, MN (US); Matthew Cambronne, Mounds View, MN (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 1098 days.

(21) Appl. No.: 11/771,731

(22) Filed: Jun. 29, 2007

(65) Prior Publication Data

US 2009/0005850 A1 Jan. 1, 2009

(51) Int. Cl.
*A61F 2/06* (2006.01)
(52) U.S. Cl. ..................................................... 623/1.15
(58) Field of Classification Search ................. 623/1.15, 623/1.2, 1.44, 1.16–1.19, 1.32, 1.33, 1.45, 623/1.46; 606/200
See application file for complete search history.

(56) References Cited

U.S. PATENT DOCUMENTS

| 2,812,270 | A | * | 11/1957 | Alexander ................. 427/178 |
|---|---|---|---|---|
| 4,800,882 | A | | 1/1989 | Gianturco |
| 5,059,205 | A | | 10/1991 | El-Nounou et al. |
| 5,091,205 | A | | 2/1992 | Fan |
| 5,226,909 | A | | 7/1993 | Evans et al. |
| 5,344,402 | A | | 9/1994 | Crocker |
| 5,344,426 | A | | 9/1994 | Lau et al. |
| 5,443,498 | A | | 8/1995 | Fontaine |
| 5,628,787 | A | | 5/1997 | Mayer |
| 5,630,840 | A | | 5/1997 | Mayer |
| 5,632,840 | A | | 5/1997 | Campbell |
| 5,755,770 | A | | 5/1998 | Ravenscroft |
| 5,824,046 | A | | 10/1998 | Smith et al. |
| 5,891,191 | A | | 4/1999 | Stinson |
| 5,916,263 | A | | 6/1999 | Goicoechea et al. |
| 5,919,570 | A | | 7/1999 | Hostettler et al. |
| 5,951,585 | A | | 9/1999 | Cathcart et al. |
| 5,957,930 | A | | 9/1999 | Vrba |
| 6,120,522 | A | | 9/2000 | Vrba et al. |
| 6,123,712 | A | | 9/2000 | DiCaprio et al. |

(Continued)

FOREIGN PATENT DOCUMENTS

| WO | 93/19803 | 10/1993 |
|---|---|---|
| WO | 95/30384 | 11/1995 |

(Continued)

OTHER PUBLICATIONS

Eisenbarth et al. "Biocompatibility of beta-stabilizing elements of titanium alloys." Biomaterials. 25 (2004) 5705-5713.

(Continued)

*Primary Examiner* — Thomas McEvoy
(74) *Attorney, Agent, or Firm* — Fish & Richardson P.C.

(57) ABSTRACT

An endoprosthesis can have a member that includes molybdenum and at least one metal selected from the group consisting of titanium, rhenium, yttrium, palladium, rhodium, ruthenium, tungsten, tantalum, iridium, zirconium, hafnium, niobium, chromium, and combinations thereof. The member can have a microstructure characterized by: (a) a molybdenum-rich base region comprising at least 50 weight percent molybdenum, (b) a surface region comprising at least one metal selected from the group consisting of titanium, rhenium, yttrium, palladium, rhodium, ruthenium, tungsten, tantalum, iridium, zirconium, hafnium, niobium, chromium, and combinations thereof, and (c) an inter-diffusion region in which the concentration of molybdenum decreases in the thickness direction from the molybdenum-rich base region to the surface region of the member.

20 Claims, 3 Drawing Sheets

U.S. PATENT DOCUMENTS

| | | | |
|---|---|---|---|
| 6,137,060 | A | 10/2000 | Avellanet |
| 6,238,491 | B1 | 5/2001 | Davidson et al. |
| 6,379,383 | B1 | 4/2002 | Palmaz et al. |
| 7,001,419 | B2 | 2/2006 | DiCaprio et al. |
| 2002/0116046 | A1 | 8/2002 | DiCaprio et al. |
| 2003/0181972 | A1 | 9/2003 | Jansen et al. |
| 2005/0059994 | A1* | 3/2005 | Walak et al. ............... 606/200 |
| 2005/0131522 | A1* | 6/2005 | Stinson et al. ............. 623/1.15 |
| 2006/0224237 | A1 | 10/2006 | Furst et al. |
| 2007/0207186 | A1* | 9/2007 | Scanlon et al. ............ 424/424 |

FOREIGN PATENT DOCUMENTS

| | | | |
|---|---|---|---|
| WO | WO 00/54704 | | 9/2000 |
| WO | WO 03/082362 | | 10/2003 |
| WO | WO 2004/022122 | | 3/2004 |
| WO | WO 2007/076376 | * | 5/2007 |

OTHER PUBLICATIONS

Authorized officer Beate Giffo-Schmitt, International Preliminary Report on Patentability in PCT/US2008/67921 mailed Jan. 14, 2010, 8 pages.

Authorized officer Almudena Montalvillo, International Search Report/Written Opinion in PCT/US2008/67921 mailed Sep. 30, 2009, 11 pages.

Karjalainen et al., "Real world experience with the TITAN® stent: a 9-month follow-up report from The Titan PORI Registry," *Eurointerv.*, 2006, 2:187-191.

Koster et al., "Nickel and molybdenum contact allergies in patients with coronary in-stent restenosis," *Lancet*, 2000, 356:1895-1897.

* cited by examiner

MOLYBDENUM ENDOPROSTHESES

TECHNICAL FIELD

This invention relates to endoprostheses, and more particularly to stents.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced, or even replaced, with a medical endoprosthesis. An endoprosthesis is typically a tubular member that is placed in a lumen in the body. Examples of endoprostheses include stents, covered stents, and stent-grafts.

Endoprostheses can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen.

The expansion mechanism can include forcing the endoprosthesis to expand radially. For example, the expansion mechanism can include the catheter carrying a balloon, which carries a balloon-expandable endoprosthesis. Balloon-expandable endoprostheses are commonly made of 316L stainless steel or L605 alloys. The balloon can be inflated to deform and to fix the expanded endoprosthesis at a predetermined position in contact with the lumen wall. The balloon can then be deflated, and the catheter withdrawn.

When the endoprosthesis is advanced through the body, its progress can be monitored, e.g., tracked, so that the endoprosthesis can be delivered properly to a target site. After the endoprosthesis is delivered to the target site, the endoprosthesis can be monitored to determine whether it has been placed properly and/or is functioning properly. Methods of monitoring a medical device include X-ray fluoroscopy, computed tomography (CT), and magnetic resonance imaging (MRI).

SUMMARY

In one aspect, an endoprosthesis is disclosed having a member that includes molybdenum and at least one metal selected from the group consisting of titanium, rhenium, yttrium, palladium, rhodium, ruthenium, tungsten, tantalum, iridium, zirconium, hafnium, niobium, chromium, and combinations thereof. The member having a microstructure characterized by: (a) a molybdenum-rich base region comprising at least 50 weight percent molybdenum, (b) a surface region comprising at least one metal selected from the group consisting of titanium, rhenium, yttrium, palladium, rhodium, ruthenium, tungsten, tantalum, iridium, zirconium, hafnium, niobium, chromium, and combinations thereof, and (c) an inter-diffusion region in which the concentration of molybdenum decreases in the thickness direction from the molybdenum-rich base region to the surface region of the member.

In some embodiments, the molybdenum base region can include no more than 10 weight percent of any of the following elements: titanium, rhenium, yttrium, palladium, rhodium, ruthenium, tungsten, tantalum, zirconium, hafnium, iridium, and chromium. In some embodiments, the molybdenum-rich base region can include at least 95 weight percent molybdenum. For example, the molybdenum-rich base region can include 1.25 weight percent titanium, 0.3 weight percent zirconium, 0.15 weight percent carbon, and a balance of molybdenum. The molybdenum-rich base region could also include between 0.25 and 1.0 weight percent titanium, between 0.04 and 2.0 weight percent zirconium, between 0.01 and 0.04 weight percent carbon, and a balance of molybdenum. In some embodiments, the molybdenum-rich base region can include 99.95% pure molybdenum doped with potassium silicate.

In some embodiments, the surface region can be essentially free of molybdenum. In other embodiments, the surface region can include less than 50 percent by weight molybdenum. In some embodiments, the surface region can include titanium. For example, the surface region can include a titanium-molybdenum alloy or can consist essentially of titanium.

In some embodiments, the inter-diffusion region can be at between 10 nanometers and 10 microns thick. In some embodiments, the inter-diffusion region is at least 1 micron thick. In some embodiments, the inter-diffusion region can include iridium. For example, inter-diffusion region can include a higher concentration of iridium than either the molybdenum-rich base region or the surface region.

In some embodiments, the member can further include oxides, carbides, nitrides, or a combination thereof overlying the surface region. For example, the oxides, carbides, and nitrides can be selected from the group consisting of zirconium oxide, hafnium oxide, chromium oxide, iridium oxide, titanium oxy-nitride, TiO2, Nb2O5, Ta2O5, and combinations thereof. In some embodiments, the member can include a coating of zirconium, hafnium, chromium, iridium, or combinations thereof overlying the surface region. In some embodiments, the member can include a drug-eluting polymer coating overlying the surface region.

In some embodiments, the member can have a modulus of between 44 and 50 msi, a 0.2% offset yield strength of at least 50 ksi, and/or an elongation to break of at least about 15%. In some embodiments, the molybdenum-rich base region can have a density of at least 9.5 g/cc.

In some embodiments, endoprosthesis can be a stent. For example, the endoprosthesis can be a balloon-expandable stent.

In another aspect, there is disclosed an endoprosthesis having a member that includes molybdenum and titanium. The member having a microstructure characterized by: (a) a molybdenum-rich base region including at least 50 weight percent molybdenum, and (b) a surface region including titanium.

In some embodiments, the surface region can consists essentially of titanium. In other embodiments, the surface region can include a titanium-molybdenum alloy.

In some embodiments, the member can further include an intermediate region comprising iridium. In some embodiments, the member can further include a coating of zirconium, hafnium, chromium, iridium, or combinations thereof overlying the surface region.

In some embodiments, the endoprosthesis can be a stent. For example, the endoprosthesis can be a balloon-expandable stent.

Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
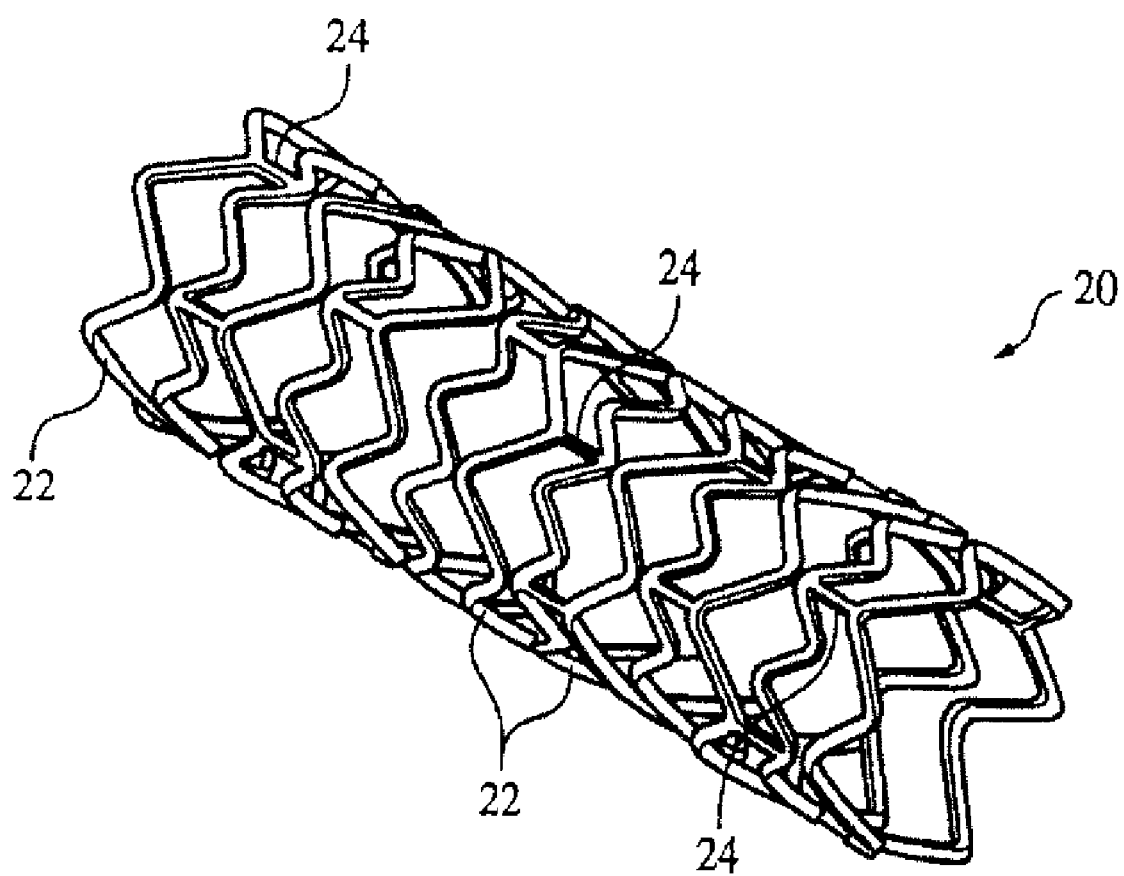
FIG. 1 is a perspective view of an embodiment of an expanded stent.

Referring to FIG. 1, a balloon-expandable stent 20 can have the form of a tubular member defined by a plurality of bands 22 and a plurality of connectors 24 that extend between and connect adjacent bands. During use, bands 22 can be expanded from an initial, smaller diameter to a larger diameter to contact stent 20 against a wall of a vessel, thereby maintaining the patency of the vessel. Connectors 24 can provide stent 20 with flexibility and conformability that allow the stent to adapt to the contours of the vessel.

The bands 22 and connectors 24 of the balloon-expandable stent 20 can include molybdenum and at least one of the following metals, alone or in combination with each other: titanium, rhenium, yttrium, palladium, rhodium, ruthenium, tungsten, tantalum, iridium, zirconium, hafnium, niobium, and chromium. Molybdenum has an advantageous combination of mechanical and physical properties, including a unique balance of modulus and yield strength. The modulus for molybdenum is higher than the modulus of 316L stainless steel and of L605 alloys, while molybdenum's yield strength is between the yield strengths of 316L stainless steel and of L605 alloys. This balance of properties would provide a lower diameter recoil for better securement on the delivery system and expanded diameter retention (apposition to the vessel wall) than 316L stainless steel and L605 alloys when used in the same stent configuration. A molybdenum stent could also be more MRI compatible because molybdenum has a lower magnetic susceptibility than iron and cobalt, which are ferromagnetic elements. Molybdenum also has higher radiopacity than 316L stainless steel and L605 alloys because molybdenum has a higher material mass absorption coefficient and a higher density. Molybdenum is commercially available in tubing form from Eagle Alloys, Goodfellow, and Minitubes. A comparison of the material properties of commercially pure molybdenum versus 316L stainless steel and L605 is presented in Table 1, below.

TABLE I

| Alloy: | Young's Modulus (E), msi | 0.2% offset yield strength, ksi | % elongation at fracture | Density, g/cc |
|---|---|---|---|---|
| Molybdenum | 44 | 70 | 20 | 10.2 |
| 316L stainless steel | 28 | 45 | 55 | 8.0 |
| L605 | 33 | 89 | 50 | 9.3 |

Figure 2:
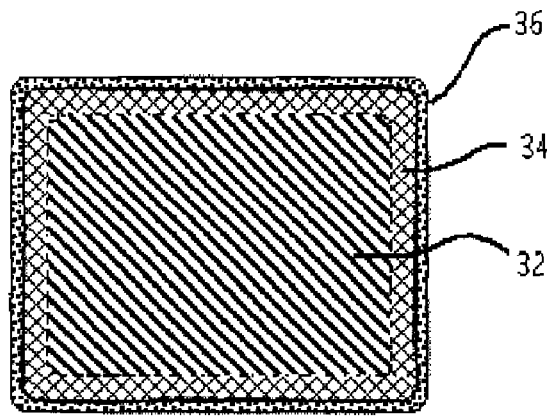
FIG. 2 is a cross sectional view of a band or connector of a stent.

FIG. 2 depicts a cross section of a band 22 or connector 24 of a stent. The member can have a microstructure that includes a molybdenum-rich base region 32, an inter-diffusion region 34, and a surface region 36. The molybdenum-rich base region 32 can include at least 50 weight percent molybdenum. The surface region 36 can include at least one of the following metals, alone or in combination with each other: titanium, rhenium, yttrium, palladium, rhodium, ruthenium, tungsten, tantalum, iridium, zirconium, hafnium, niobium, and chromium. The inter-diffusion region 34 can include a varying concentration of molybdenum, which decreases in the thickness direction from the molybdenum-rich base region to the surface region of the member.

The molybdenum-rich base region 32 can include at least 50 weight percent molybdenum, but can also include other metals, such as titanium, rhenium, yttrium, palladium, rhodium, ruthenium, tungsten, tantalum, zirconium, hafnium, iridium, and/or chromium. In some embodiments, the molybdenum-rich base region 32 can be limited to no more than 10 weight percent of any of these elements. The molybdenum-rich base region can have a density of at least 9.5 g/cc.

In some embodiments, the molybdenum-rich base region can have a molybdenum concentration of at least 95 weight percent. For example, the molybdenum-rich base region can include Mo TZM, Mo TZC, or Mo HCT alloys. Mo TZC alloy includes 1.25 weight percent titanium, 0.3 weight percent zirconium, 0.15 weight percent carbon, and a balance of essentially molybdenum. Mo TZM alloy includes between 0.25 and 1.0 weight percent titanium, between 0.04 and 2.0 weight percent zirconium, between 0.01 and 0.04 weight percent carbon, and a balance of essentially molybdenum. Mo HCT, from Elmet Technologies, includes 99.95% pure Mo doped with potassium silicate. Mo HCT can have a maximum of 150 ppm potassium, a maximum of 300 ppm silicon, and a maximum of 200 ppm oxygen. HCT stands for High reCrystallization Temperature. The properties for Mo HCT are essentially the same as for pure Mo, but the benefit of using Mo HCT is that it allows for diffusion heat treatment at higher temperatures than for pure Mo and thus it can allow for interdiffusion in shorter processing times. The material properties of Mo TZC and Mo TZM are included below in Table II.

TABLE II

| Alloy: | Ultimate Tensile Strength, ksi | Yield Strength, ksi | Elongation, % | Modulus, msi | Density, g/cc |
|---|---|---|---|---|---|
| MoTZC | 144 | 105 | 22 | 47 | 10.1 |
| MoTZM | 140 | 125 | 10 | 47 | 10.2 |

The surface region 36 can include at least one of the following metals, alone or in combination with each other: titanium, rhenium, yttrium, palladium, rhodium, ruthenium, tungsten, tantalum, iridium, zirconium, hafnium, niobium, and chromium. The surface region can enhance corrosion resistance and/or improve the biocompatibility of the stent. In some embodiments, the surface region can be essentially free of molybdenum. In other embodiments, the surface region can include molybdenum in amounts lower than 50 percent by weight. In some embodiments, the surface region can include titanium. For example, the surface region can include essentially pure titanium or can include a titanium-molybdenum alloy.

The microstructure can also include an inter-diffusion region in which the concentration of molybdenum decreases in the thickness direction from the molybdenum-rich base region to the surface region of the member. In some embodiments, the inter-diffusion region can be at least 1 micron thick. In some embodiments, the inter-diffusion region can be between 10 nanometers and 10 microns. The inter-diffusion region can include a mixture of the constituents of the surface region 36 and the molybdenum-rich base region 32 with a concentration gradient transitioning from a region of higher molybdenum concentration adjacent to the molybdenum-rich base region 32 to a lower molybdenum concentration adjacent to the surface region 36.

Figure 3:
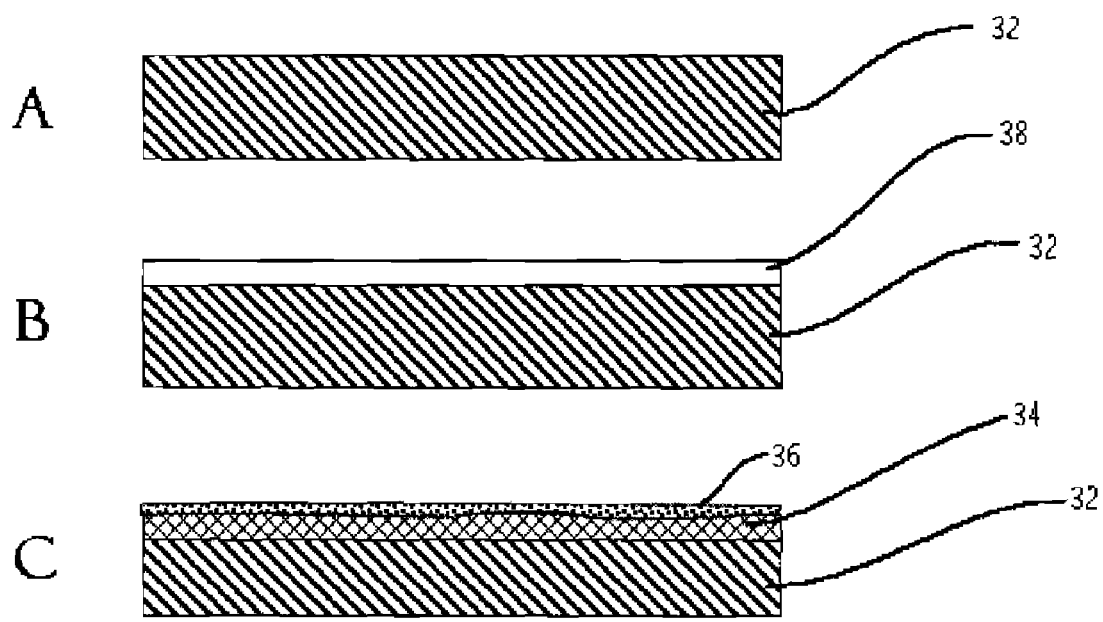
FIGS. 3A-3C depict a process for producing a member having an inter-diffusion region between a molybdenum-rich base region and a surface region.

FIGS. 3A-3C depict an exemplary method for producing a member having a molybdenum-rich base region 32, a surface region 36, and an inter-diffusion region 34 therebetween. For example, as shown in FIG. 3A, a molybdenum-rich substrate 32 having at least 50 weight percent molybdenum can be provided. The substrate 32 can be cleaned in a plasma vapor deposition coating chamber with an oxide reduction process using an argon-hydrogen plasma.

As shown in FIG. 3B, a layer of a second metal 38 can be deposited onto the substrate 32. The second material 38 can include titanium, rhenium, yttrium, palladium, rhodium, ruthenium, tungsten, tantalum, iridium, zirconium, hafnium, niobium, or chromium. The second material 38 can be deposited using conventional plasma deposition equipment. The second material 38 can form a deposit of up to about 20 microns thick (e.g., between 20 nanometers and 1 micron thick). The layer of second material 38 can also be deposited by other commercially available ion implantation, sputter coating, chemical vapor deposition, or electroplating methods.

As shown in FIG. 3C, the inter-diffusion region can be created by applying a surface-alloying diffusion treatment. For example, a heat treatment can be performed in high vacuum at greater than about $10^{-5}$ torr. The heat treatment can be performed at a temperature selected from the range of 100° C. below the molybdenum tubing recrystallization temperature to 100° C. above the recrystallization temperature for 30 to 240 minutes. During this thermal exposure, the molybdenum and second metal would interdiffuse and produce an alloy of the constituents of the molybdenum-rich substrate 32 and the second material 38. The resulting surface region 36 can either be made up entirely of the second material 38 or can include molybdenum diffused from the molybdenum-rich substrate 32. The surface of the stent can contain 0 to 50% molybdenum, which can be controlled by controlling the extent of inter-diffusion. For example, the diffusivity of molybdenum in titanium at 1,000° C. was calculated to be 5.852 $\mu^2$/second and at 1,200° C. was calculated to be 294.5 $\mu^2$/second. The diffusion treatment can also convert a work hardened molybdenum-rich substrate to a condition of lower strength and higher ductility.

The tensile properties of the diffusion treated surface alloyed stent material, such as that shown in FIG. 2, would be between 44 and 50 msi Young's modulus, between 50 and 80 ksi 0.2% offset yield strength, between 65 and 95 ksi ultimate tensile strength, and/or greater than 15 percent elongation to break.

In some embodiments, the surface region 36 can be essentially pure titanium. In other embodiments, the surface region 36 comprises a titanium-molybdenum alloy. A titanium-molybdenum alloy can include up to about 50 weight percent molybdenum, and in some embodiments can contain less than 40 weight percent molybdenum. In some embodiments, a titanium containing surface region 36 can also include rhenium, yttrium, palladium, rhodium, ruthenium, tungsten, tantalum, iridium, zirconium, hafnium, niobium, and/or chromium as additional alloying elements.

In some embodiments, the surface region 36 can further be converted to oxides, nitrides, carbides, or combinations thereof. In some embodiments, zirconium, hafnium, iridium, or chromium can further be applied to the surface region 36 and converted to an oxide. If the surface region 36 includes titanium and the air atmosphere were supplemented with a partial pressure of nitrogen, titanium oxynitride can form on the surface region 36 instead of titanium oxide. Titanium oxynitride may have a pro-healing response to minimize restenosis. In some embodiments, the surface can include $TiO_2$, $Nb_2O_5$ and/or $Ta_2O_5$. An alternate method could be to use electrochemical anodizing to build an oxide layer rather than thermal treatment methods.

In some embodiments, the stent can include iridium and/or iridium oxide. For example, iridium can be applied to a molybdenum base metal and converted into an iridium oxide. Iridium can also be present as an intermediate alloying constituent present in the inter-diffusion region 34. In some embodiments, a stent can include a molybdenum base metal, a concentration gradient transitioning from the molybdenum base metal to iridium or an alloy thereof, and a concentration gradient transitioning from iridium or an alloy thereof to titanium or an alloy thereof. The intermediate iridium or iridium alloy can be between about 5 to 10 microns thick in order to prevent small cracks from reaching the molybdenum base metal.

In some embodiments, a drug eluting polymer coating can also be applied to the surface region 36. For example, drug eluding polymer coatings include those described in U.S. Pat. No. 5,674,242, U.S. Ser. No. 09/895,415, filed Jul. 2, 2001, and U.S. Ser. No. 10/232,265, filed Aug. 30, 2002. The therapeutic agents, drugs, or pharmaceutically active compounds can include, for example, anti-thrombogenic agents, antioxidants, anti-inflammatory agents, anesthetic agents, anti-coagulants, and antibiotics.

Figure 4:
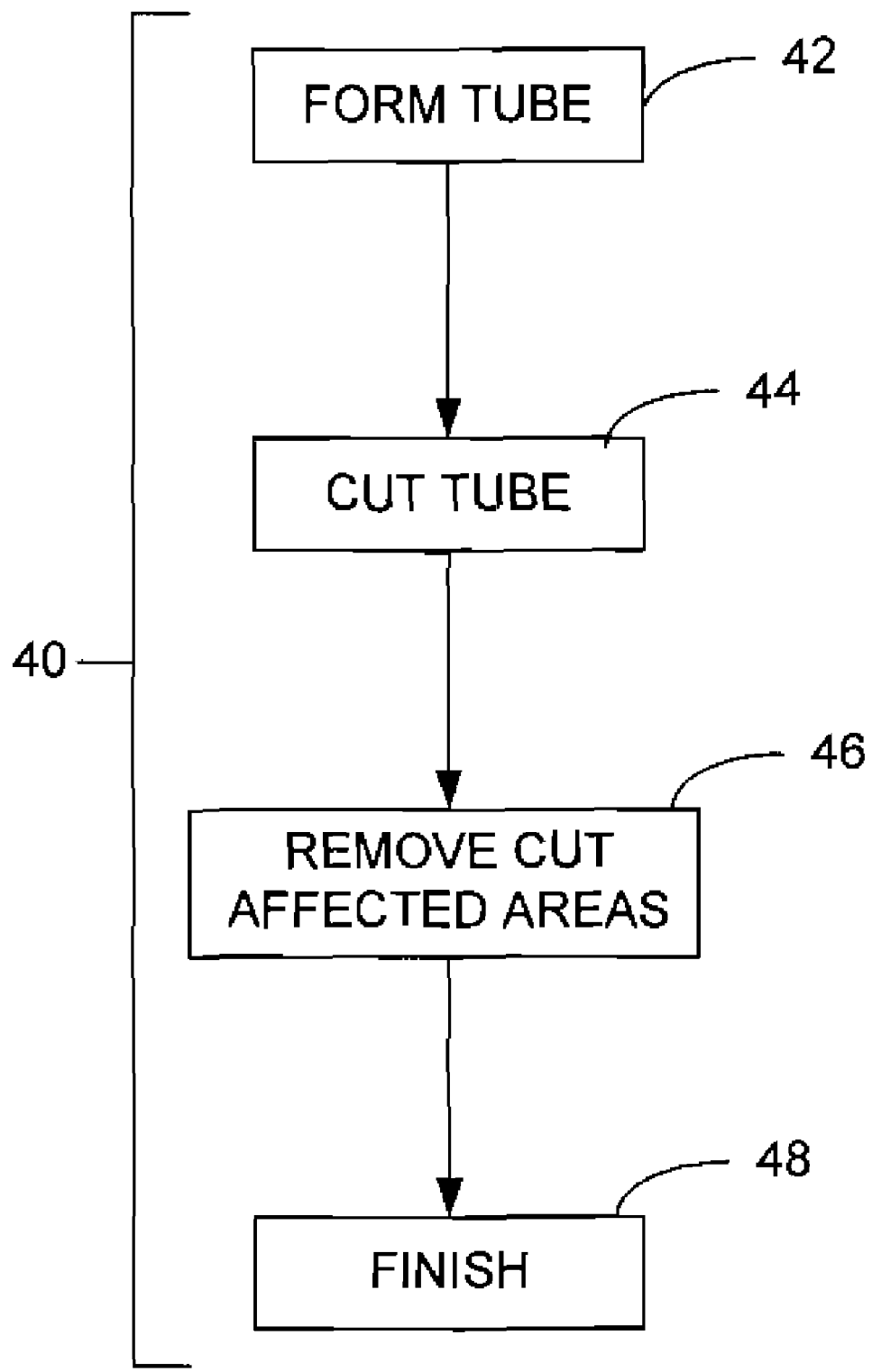
FIG. 4 is a flow chart of an embodiment of a method of making a stent.

FIG. 4 shows an example of a method 40 of making a stent 20. As shown, method 40 can include forming a tube (step 42) that includes molybdenum or a molybdenum alloy. The tube can be subsequently cut to form bands 22 and connectors 24 (step 44) to produce an unfinished stent. Areas of the unfinished stent affected by the cutting can be subsequently removed (step 46). The unfinished stent can be finished by applying a second material and heat treating to form a stent 20 having a molybdenum-rich base region 32, a surface region 36, and an inter-diffusion region 34 (step 48).

For example, a stent can be made from a hollow rod of molybdenum or a molybdenum alloy. The hollow rod can have an outer diameter of 0.8 to 1.2 inches and an inner diameter of 0.4 to 0.6 inches and a length of 6 to 9 inches. The hollow rod could be conventionally canned and hot-extruded to reduce the wall thickness to about 0.05 inches. The tube can be reduced in size via fixed mandrel or floating plug tube drawing operations with intermediate stress relieving steps to the final configuration of a 0.060 to 0.080 inch outer diameter and a 0.050 to 0.070 inch inner diameter (depending on the desired finished stent size). The stent tubing can be subjected to laser machining to cut the stent bands 22 and connectors 24 in the wall. Electrochemical etching and polishing can be used to remove the laser-affected layer of material, to produce the final dimensions of the stent substrate 32, and to produce a smooth surface texture. The stent substrate 32 would then be subject to the deposition and diffusion treatments as discussed above in regard to FIGS. 3A-3C to produce a stent having bands 22 and/or connectors 24 having a molybdenum-rich base region 32, a surface region 36, and an inter-diffusion region 34 as shown in FIG. 2. The finished molybdenum containing stent can be crimped onto a balloon catheter, packaged, and sterilized.

Stent 20 can be of a desired shape and size (e.g., coronary stents, aortic stents, peripheral vascular stents, gastrointestinal stents, urology stents, and neurology stents). Depending on the application, stent 20 can have a diameter of between, for example, 1 mm to 46 mm. In certain embodiments, a coronary stent can have an expanded diameter of from 2 mm to 6 mm. In some embodiments, a peripheral stent can have an expanded diameter of from 5 mm to 24 mm. In certain embodiments, a gastrointestinal and/or urology stent can have an expanded diameter of from 6 mm to about 30 mm. In some embodiments, a neurology stent can have an expanded diameter of from about 1 mm to about 12 mm. An abdominal aortic aneurysm (AAA) stent and a thoracic aortic aneurysm (TAA) stent can have a diameter from about 20 mm to about 46 mm.

For example, a molybdenum-containing bare-metal balloon-expandable coronary stent can have a wall thickness of 0.0030 inches. Such a balloon-expandable stent can have a diameter recoil of less than 6 percent upon balloon expansion to 3.2 mm diameter. The stent can require between 0.20 and 0.40 Newtons force per millimeter of stent length to compress it from an initial balloon expanded diameter of 3.2 mm to 2.75 mm diameter oval within a V-shaped platens compression tester.

In use, stent 20 can be used, e.g., delivered and expanded, using a catheter delivery system. Catheter systems are described in, for example, Wang U.S. Pat. No. 5,195,969, Hamlin U.S. Pat. No. 5,270,086, and Raeder-Devens, U.S. Pat. No. 6,726,712. Stents and stent delivery are also exemplified by the Sentinol® system, available from Boston Scientific Scimed, Maple Grove, Minn.

In some embodiments, a stent can be fabricated by forming a wire including a molybdenum-rich base region 32, a surface region 36, and an inter-diffusion region 34, and knitting and/or weaving the wire into a tubular member.

Stent 20 can also be a part of a covered stent or a stent-graft. For example, stent 20 can include and/or be attached to a biocompatible, non-porous or semi-porous polymer matrix made of polytetrafluoroethylene (PTFE), expanded PTFE, polyethylene, urethane, or polypropylene.

The molybdenum containing members described herein can be used to form other endoprostheses. For example, the molybdenum containing members can be used to form a guidewire or a hypotube. The molybdenum members can also be used to form metal staples and wires used for wound closure.

All publications, references, applications, and patents referred to herein are incorporated by reference in their entirety.

Other embodiments are within the claims.

What is claimed is:

1. An endoprosthesis comprising a member that includes molybdenum and at least one metal selected from the group consisting of titanium, rhenium, yttrium, palladium, rhodium, ruthenium, tungsten, tantalum, iridium, zirconium, hafnium, niobium, chromium, and combinations thereof,
    the member having a microstructure characterized by:
        (a) a molybdenum-rich base region comprising at least 50 weight percent molybdenum,
        (b) a surface region comprising molybdenum and at least one metal selected from the group consisting of titanium, rhenium, yttrium, palladium, rhodium, ruthenium, tungsten, tantalum, iridium, zirconium, hafnium, niobium, chromium, and combinations thereof, and
        (c) an inter-diffusion region in which the concentration of molybdenum decreases in the thickness direction from the molybdenum-rich base region to the surface region of the member, wherein the inter-diffusion region comprises a higher concentration of iridium than either the molybdenum-rich base region or the surface region.

2. The endoprosthesis of claim 1, wherein the molybdenum-rich base region comprises no more than 10 weight percent of any of the following elements: titanium, rhenium, yttrium, palladium, rhodium, ruthenium, tungsten, tantalum, zirconium, hafnium, iridium, and chromium.

3. The endoprosthesis of claim 1, wherein the member has a modulus of between 44 and 50 msi.

4. The endoprosthesis of claim 1, wherein the member has a 0.2% offset yield strength of at least 50 ksi.

5. The endoprosthesis of claim 1, wherein the member has an elongation to break of at least about 15%.

6. The endoprosthesis of claim 1, wherein the molybdenum-rich base region has a density of at least 9.5 g/cc.

7. The endoprosthesis of claim 1, wherein the molybdenum-rich base region comprises at least 95 weight percent molybdenum.

8. The endoprosthesis of claim 7, wherein the molybdenum-rich base region comprises 1.25 weight percent titanium, 0.3 weight percent zirconium, 0.15 weight percent carbon, and a balance of molybdenum.

9. The endoprosthesis of claim 7, wherein the molybdenum-rich base region comprises between 0.25 and 1.0 weight percent titanium, between 0.04 and 2.0 weight percent zirconium, between 0.01 and 0.04 weight percent carbon, and a balance of molybdenum.

10. The endoprosthesis of claim 7, wherein the molybdenum-rich base region comprises 99.95% pure molybdenum doped with potassium silicate.

11. The endoprosthesis of claim 1, wherein the surface region comprises less than 50 percent by weight molybdenum.

12. The endoprosthesis of claim 1, wherein the surface region comprises titanium.

13. The endoprosthesis of claim 1, wherein the inter-diffusion region is between 10 nanometers and 10 microns thick.

14. The endoprosthesis of claim 1, wherein the inter-diffusion region is at least 1 micron thick.

15. The endoprosthesis of claim 1, wherein the member further comprises oxides, carbides, nitrides, or a combination thereof overlying the surface region.

16. The endoprosthesis of claim 15, wherein the oxides, carbides, and nitrides are selected from the group consisting of zirconium oxide, hafnium oxide, chromium oxide, iridium oxide, titanium oxy-nitride, $TiO_2$, $Nb_2O_5$, $Ta_2O_5$, and combinations thereof.

17. The endoprosthesis of claim 1, further comprising a coating of zirconium, hafnium, chromium, iridium, or combinations thereof overlying the surface region.

18. The endoprosthesis of claim 1, further comprising a drug-eluting polymer coating overlying the surface region.

19. The endoprosthesis of claim 18, wherein the endoprosthesis is a balloon-expandable stent.

20. The endoprosthesis of claim 1, wherein the endoprosthesis is a stent.

* * * * *